United States Patent [19]

Inoue et al.

[11] Patent Number: 5,238,837
[45] Date of Patent: Aug. 24, 1993

[54] SUPEROXIDE DISMUTASE DERIVATIVES

[75] Inventors: Masayasu Inoue, 49-3, Ikeda 3-chome, Kumamoto-city, Kumamoto; Iwao Ebashi; Tetsuo Takigawa, both of Kurashiki, all of Japan

[73] Assignees: Kuraray Co., Ltd., Kurashiki; Masayasu Inoue, Kumamoto, both of Japan

[21] Appl. No.: 803,414

[22] Filed: Dec. 6, 1991

[30] Foreign Application Priority Data

Feb. 5, 1991 [JP] Japan .................................. 3-36765

[51] Int. Cl.$^5$ .............................................. C12N 9/02
[52] U.S. Cl. .................................. 435/189; 424/94.3; 424/94.4; 435/188
[58] Field of Search ............... 435/189, 188; 424/94.4, 424/94.3

[56] References Cited

U.S. PATENT DOCUMENTS 4,801,538  1/1989  Hanada et al. ..................... 435/192

FOREIGN PATENT DOCUMENTS

| 0292964 | 11/1988 | European Pat. Off. ............ 435/189 |
| 0426488 | 5/1991  | European Pat. Off. ............ 435/189 |
| 1095774 | 4/1989  | Japan ................................. 435/189 |
| 1096107 | 4/1989  | Japan ................................. 435/189 |
| 1250304 | 10/1989 | Japan ................................. 435/189 |
| 1257479 | 10/1989 | Japan ................................. 435/189 |
| 2231075 | 9/1990  | Japan ................................. 435/189 |
| 2231076 | 9/1990  | Japan . |
| 2231078 | 9/1990  | Japan . |
| 2231277 | 9/1990  | Japan . |
| 2273176 | 11/1990 | Japan ................................. 435/189 |

OTHER PUBLICATIONS

Pierce 1989 Handbook & Catalogue P.O. Box 117 Rockford, Ill. 61105 pp. 296–297.
M. Inoue et al, *Biochemistry*, vol. 28, pp. 6619–6624 (1989).
Chemical Abstracts, vol. 115(5), abstract 43323t (1991).
Chemical Abstracts, vol. 112(14), abstract 125189f (1990).

*Primary Examiner*—Herbert J. Lilling
*Attorney, Agent, or Firm*—Burns, Doane, Swecker & Mathis

[57] ABSTRACT

Provided are novel superoxide dismutase derivatives represented by the following general formula (I)

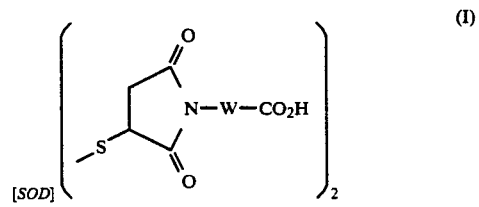

wherein [SOD] is a superoxide dismutase residue derived by removal of two mercapto groups, and W is a divalent long chain hydrocarbon residue which may optionally be interrupted by one or more groups each independently selected from the group consisting of an oxygen atom, a sulfur atom and a group of —N(R)— (R being a lower alkyl group). The SOD derivatives retain most of the enzymatic activities of unmodified SOD and have much longer plasma half-life than unmodified SOD. They are effective for treating various diseases caused by active oxygen species.

Also provided are chemical modifiers to prepare the above SOD derivatives.

3 Claims, 7 Drawing Sheets

SUPEROXIDE DISMUTASE DERIVATIVES

BACKGROUND OF THE INVENTION

1. Field of the Invention

The present invention relates to superoxide dismutase derivatives.

The superoxide dismutase derivatives provided by the present invention retain most of the enzymatic activities of superoxide dismutase capable of decomposing superoxide, which is harmful to living organisms, and have an extremely prolonged plasma half-life as compared with the superoxide dismutase. Also, the superoxide dismutase derivatives of the present invention are effective for treating various diseases caused by active oxygen species, and can be used as anti-inflammatory agents, anti-ulcer agents, anti-ischemic agents, cerebral edema-treating agents and paraquat intoxication-treating agents. Further, the superoxide dismutase derivatives are useful for drugs for alleviating various side effects induced by anti-cancer agents, as caused by active oxygen species.

The present invention also relates to chemical modifiers to provide the above-mentioned superoxide dismutase derivatives.

2. Description of the Prior Art

Superoxide dismutase (hereinafter sometimes referred to as "SOD") is known as an enzyme occurring widely in living organisms, such as animals, plants and microorganisms, and decomposing superoxide which is harmful to living organisms. In recent years, attempts have been made to use SOD as an anti-inflammatory agent [Farumashia, 17, 411–412 (1981); Current Therapeutic Research, 16, 706 (1974)]; as a protective agent for cardiac surgery [Furii Rajikaru no Rinsho (Clinical Medicine on Free Radical), Vol. 5, 113-119, Nihon Igakukan, issued on Nov. 30, 1990]. It is said that the plasma half-life of intravenously administered SOD is only 4 to 6 minutes; that is, SOD is rapidly metabolized and excreted into urine since the molecular weight of SOD (about 32,000) is smaller than the glomerular filtration limit (corresponding to a molecular weight of about 50,000). For the purpose of prolonging the plasma half-life of SOD, attempts have been made to modify SOD with natural polymers and synthetic organic compounds.

SOD derivatives modified with natural polymers such as Ficoll, inulin, dextran sulfate, dextran, heparin, hyaluronic acid, and glycosaminoglycan are known [Proc. Natl. Acad. Sci. USA, 77, 1159 (1980); Japanese Patent Application Laid-open Nos. 32826/1983, 231075/1990, 231076/1990, 231077/1990, 231078/1990 and 273176/1990]. However, these SOD derivatives do not have a definite molecular weight since each of the natural polymers has a certain distribution in its molecular weight. Rat albumin-modified SOD has also been reported, but it has antigenicity [Agents and Actions, 10, 231 (1980)].

SOD derivatives modified with synthetic polymers such as polyethylene glycol and polyalkylene glycol are known as well [Res. Commun. Chem. Pathol. Pharmacol., 29, 113 (1980); Japanese Patent Application Laid-open No. 249388/1986]. However, each of the synthetic polymers also has a certain molecular weight distribution.

Modification of SOD with a partially half-esterified styrene-maleic anhydride copolymer (hereinafter referred to as "SMA") has been investigated [Japanese Patent Application Laid-open No. 104164/1989]. The SOD derivative modified with SMA (hereinafter referred to as "SMA-SOD") has a prolonged plasma half-life because it binds reversibly plasma protein, especially albumin, and further accumulates, due to the presence of carboxylic acid groups in SMA, in regions made acidic by inflammation. Other SOD derivatives in which two SOD molecules are crosslinked via a dicarboxylic acid and which have a narrower molecular weight distribution are also known [Japanese Patent Application Laid-open No. 95775/1989], but they can hardly be expected to accumulate in inflammatory regions.

All of the above SOD derivatives have been modified by using the amino groups of SOD. Human-type SOD has 22 or 24 amino groups per molecule, while bovine-type SOD has 20 amino groups per molecule. Since SOD thus has a number of amino groups, it is very difficult to specify which amino groups of SOD have reacted with the modifier used. In view of the current situation in which the compound to be used as a medicinally active ingredient should preferably have a definite single chemical structure, it is preferred that SOD derivatives to be used for medicinal purposes should have been modified at specific sites in the molecule thereof.

From these points of view, an SOD derivative modified, via its mercapto groups, by an SMA modified with a functional group reactive with mercapto group (hereinafter referred to as "SMI-SOD") has been prepared [Japanese Patent Application Laid-open No. 257479/1989]. The plasma halflife, enzymatic activities and accumulation property in acidic regions of this SOD derivative are similar to those of above-described SMA-SOD. Moreover, this SOD derivative has definite modification sites in the SOD molecule. However, the structure of SMA is, although specified from the viewpoint of polymer chemistry, still complicated and the SMI-SOD therefore has problems in view of the abovedescribed utility as a medicinally active ingredient.

Accordingly, there has been strongly demanded development of an SOD derivative whose plasma half-life, enzymatic activities and accumulation property in acidic regions are similar to those of SMA-SOD and SMI-SOD, and which is modified at specific sites in the SOD molecule and with a modifier having a definite chemical structure.

It is an object of the present invention to provide a novel SOD derivative which is prepared by bonding a long chain carboxylic acid maleimide to each of two mercapto groups in the SOD molecule and has a significantly prolonged plasma half-life as compared with that of unmodified SOD, the characteristic of accumulating in acidic regions and a definite single chemical structure.

It is another object of the invention to provide a novel long chain carboxylic acid maleimide useful as a chemical modifier for SOD.

SUMMARY OF THE INVENTION

The present invention provides a superoxide dismutase derivative (hereinafter referred to as "SOD derivative") represented by the following general formula (I)

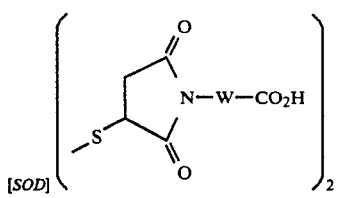

(I)

wherein [SOD] is a superoxide dismutase residue derived by removal of two mercapto groups, and W is a divalent long chain hydrocarbon residue which may optionally be interrupted by one or more groups each independently selected from the group consisting of an oxygen atom, a sulfur atom and a group of —N(R)— (R being a lower alkyl group).

Further the present invention provides a long chain carboxylic acid maleimide (hereinafter referred to as "long chain carboxylic acid maleimide (II)") represented by the following general formula (II)

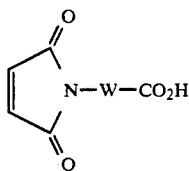

(II)

wherein W is a divalent long chain hydrocarbon residue which may optionally be interrupted by one or more groups each independently selected from the group consisting of an oxygen atom, a sulfur atom and a group of —N(R)— (R being a lower alkyl group).

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
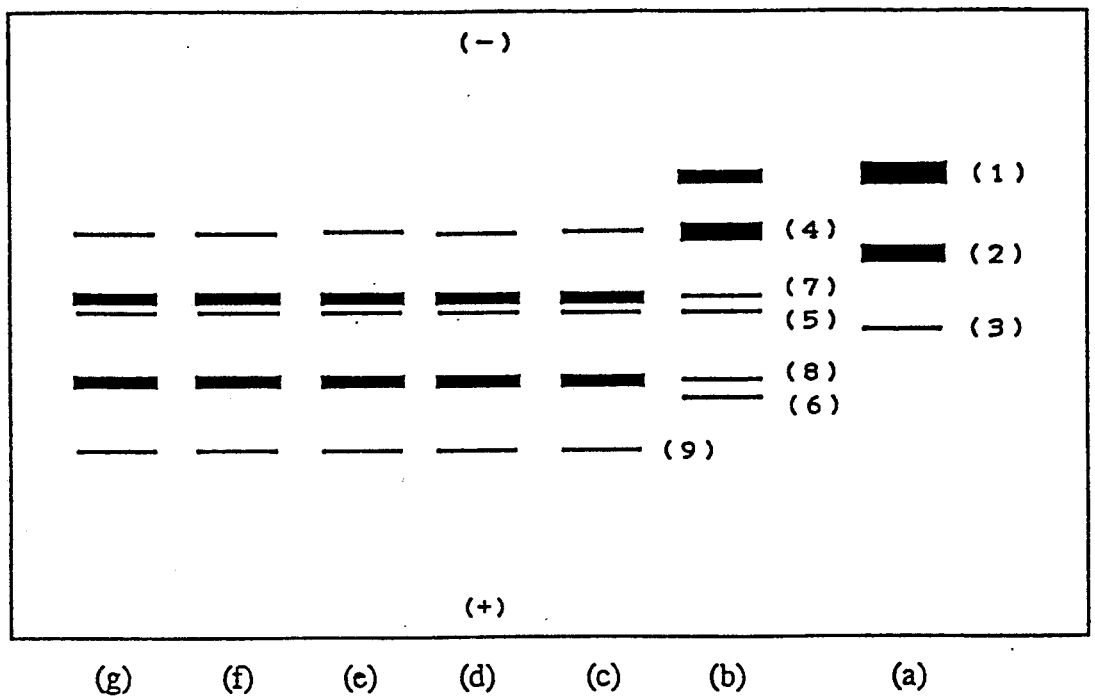
FIG. 1 shows schematic electrophorograms of the reaction mixtures obtained in Example 4, wherein diagrams (a), (b), (c), (d), (e), (f) and (g) correspond to the cases where the mole ratio of 18-maleimidooctadecanoic acid to SOD are 0, 1, 2, 5, 10, 20 and 50 respectively.

The SOD derivatives provided by the present invention can be produced by the reaction of SOD with a long chain carboxylic acid maleimide (II) in an aqueous solution maintained at a pH in a range of 6 to 10.

The reaction of SOD and a long chain carboxylic acid maleimide (II) is generally carried out by dissolving SOD in tris(hydroxymethyl)aminomethane-hydrochloric acid buffer, or in an aqueous solution of a salt such as sodium carbonate, sodium hydrogen carbonate, sodium acetate, or sodium phosphate, and adding, to the thus obtained solution, the long chain carboxylic acid maleimide (II) in the form of powder or a solution in an organic solvent such as dimethyl sulfoxide.

It is necessary that the pH of the solution should be maintained at 6 to 10, preferably 8 to 10 during the reaction. When the pH is lower than 6, the solubility of the long chain carboxylic acid maleimide (II) decreases and the reaction can hardly proceed. When the pH is higher than 10, the long chain carboxylic acid maleimide (II) tends to react also with amino groups in SOD. The reaction temperature is preferably maintained at room temperature or below. The reaction period should be selected, depending on the mode of addition of the long chain carboxylic acid maleimide (II), from the range of 10 minutes to 2 days. The long chain carboxylic acid maleimide (II) is used for the reaction in an amount of about 2.0 to 30 moles per mole of SOD.

The reaction mixture thus obtained contains the SOD derivative, unreacted SOD and the long chain carboxylic acid maleimide (II), etc. The reaction mixture is filtered, and the filtrate is subjected to gel filtration. If necessary, the thus obtained SOD derivative-containing eluate is subjected to hydrophobic column chromatography, ion-exchange column chromatography or the like, and is then concentrated by ultrafiltration. The subsequent lyophilization of the concentrate gives the SOD derivative in a solid form.

In the above reaction, two mercapto groups of SOD add to the double bond of the maleimide ring of the long chain carboxylic acid maleimide (II), whereby the SOD derivative is formed.

Examples of the divalent long chain hydrocarbon residue represented by W in the SOD derivatives of the present invention are as follows.

$(CH_2)_{17}$, $(CH_2)_{18}$, $(CH_2)_{19}$, $(CH_2)_{20}$, $(CH_2)_{21}$,
$(CH_2)_8CH=CH(CH_2)_7$, $(CH_2)_9CH=CH(CH_2)_7$,
$(CH_2)_{10}CH=CH(CH_2)_7$, $(CH_2)_{11}CH=CH(CH_2)_7$,
$(CH_2)_{12}CH=CH(CH_2)_7$, $(CH_2)_8CH=CH(CH_2)_8$,
$(CH_2)_8CH=CH(CH_2)_9$, $(CH_2)_8CH=CH(CH_2)_{10}$,
$(CH_2)_8CH=CH(CH_2)_{11}$,
$(CH_2)_5CH=CHCH_2CH=CH(CH_2)_7$,
$(CH_2)_6CH=CHCH_2CH=CH(CH_2)_7$,
$(CH_2)_7CH=CHCH_2CH=CH(CH_2)_7$,
$(CH_2)_8CH=CHCH_2CH=CH(CH_2)_7$,
$(CH_2)_9CH=CHCH_2CH=CH(CH_2)_7$,
$(CH_2)_2-O-(CH_2)_{15}$, $(CH_2)_2-O-(CH_2)_{16}$,
$(CH_2)_2-O-(CH_2)_{17}$, $(CH_2)_2-O-(CH_2)_{18}$,
$(CH_2)_2-O-(CH_2)_{18}$, $(CH_2)_4-O-(CH_2)_{13}$,
$(CH_2)_4-O-(CH_2)_{14}$, $(CH_2)_4-O-(CH_2)_{15}$,
$(CH_2(4-O-(CH_2)_{16}$, $(CH_2(4-O-(CH_2)_{17}$,
$(CH_2)_6-O-(CH_2(_{11}$, $(CH_2)_6-O-(CH_2)_{12}$,
$(CH_2)_8-O-(CH_2)_{13}$, $(CH_2(6-O-(CH_2)_{14}$, (CH₂)₆—O—(CH₂)₁₅,
(CH₂)₈—O—(CH₂)₁₀,
(CH₂(8—O—(CH₂)₁₂,
(CH₂(10—O—(CH₂)₇,
(CH₂)₁₀—O—(CH₂)₁₁,
(CH₂)₁₂—O—(CH₂)₇,
(CH₂)₂—O—(CH₂)₅CH=CH(CH₂)₇,
(CH₂)₄—O—(CH₂)₅CH=CH(CH₂)₇,
(CH₂)₆—O—(CH₂)₅CH=CH(CH₂)₇,
(CH₂)₂—S—(CH₂)₁₅,
(CH₂)₂—S—(CH₂)₁₇,
(CH₂)₂—S—(CH₂)₁₉,
(CH₂)₄—S—(CH₂)₁₄,
(CH₂)₄—S—(CH₂)₁₆,
(CH₂)₆—S—(CH₂)₁₁,
(CH₂)₆—S—(CH₂)₁₃,
(CH₂)₆—S—(CH₂)₁₅,
(CH₂)₈—S—(CH₂)₁₀,
(CH₂)₈—S—(CH₂)₁₂,
(CH₂)₁₀—S—(CH₂)₇,
(CH₂)₁₀—S—(CH₂)₁₁,
(CH₂)₁₂—S—(CH₂)₇,
(CH₂)₂—N(CH₃)—(CH₂)₁₄,
(CH₂)₂—N(C₂H₅)—(CH₂)₁₄,
(CH₂)₂—O—(CH₂)₂—O—(CH₂)₁₂, (CH₂)₄—O—(CH₂)₂—O—(CH₂)₁₂, (CH₂)₆—O—(CH₂)₂—O—(CH₂)₁₂, (CH₂)₂—O—(CH₂)₂—O—(CH₂)₁₄, (CH₂)₂—O—(CH₂)₂—O—(CH₂)₁₆,
(CH₂)₂—S—S—(CH₂)₁₆,
(CH₂)₄—S—S—(CH₂)₁₂,
(CH₂)₄—S—S—(CH₂)₁₆,
(CH₂)₆—S—S—(CH₂)₁₂,
(CH₂)₈—S—S—(CH₂)₈,
(CH₂(8—S—S—(CH₂)₁₂

(CH₂)₈—O—(CH₂)₉,
(CH₂)₈—O—(CH₂)₁₁,
(CH₂)₈—O—(CH₂)₁₃,
(CH₂)₁₀—O—(CH₂)₉,
(CH₂)₁₂—O—(CH₂)₅,
(CH₂)₁₂—O—(CH₂)₉, (CH₂)₂—S—(CH₂)₁₆,
(CH₂)₂—S—(CH₂)₁₈,
(CH₂)₄—S—(CH₂)₁₃,
(CH₂)₄—S—(CH₂)₁₅,
(CH₂)₄—S—(CH₂)₁₇,
(CH₂)₆—S—(CH₂)₁₂,
(CH₂)₆—S—(CH₂)₁₄,
(CH₂)₈—S—(CH₂)₉,
(CH₂)₈—S—(CH₂)₁₁,
(CH₂)₈—S—(CH₂)₁₃,
(CH₂)₁₀—S—(CH₂)₉,
(CH₂)₁₂—S—(CH₂)₅,
(CH₂)₁₂—S—(CH₂)₉,
(CH₂)₄—N(CH₃)—(CH₂)₁₄,
(CH₂)₆—N(CH₃)—(CH₂)₁₄,
(CH₂)₄—N(C₂H₅)—(CH₂)₁₄,
(CH₂)₆—N(C₂H₅)—(CH₂)₁₄, (CH₂)₂—S—S—(CH₂)₁₄,
(CH₂)₂—S—S—(CH₂)₁₈,
(CH₂)₄—S—S—(CH₂)₁₄,
(CH₂)₆—S—S—(CH₂)₁₀,
(CH₂)₆—S—S—(CH₂)₁₄,
(CH₂)₈—S—S—(CH₂)₁₀,

The long chain carboxylic acid maleimide (II) has one maleimide group per molecule, and human-type SOD has two reactive mercapto groups. Therefore, the above-described reaction and the succeeding treatment steps can give an SOD derivative comprising two molecules of the long chain carboxylic acid maleimide (II) bonded to one molecule of human-type SOD. In the above reaction and the succeeding treatment steps, the carboxyl groups of the SOD derivative might each possibly form an alkali metal salt or an ammonium salt. The SOD derivative of the present invention includes such SOD derivative containing the carboxyl groups in a salt form as well.

The SOD derivatives of the present invention are obtained by bonding two molecules of the long chain carboxylic acid maleimide (II) to one SOD molecule and have an extremely prolonged plasma half-life as compared to unmodified SOD and the feature of good delivery to inflammatory regions based on their tendency to accumulate in acidic regions.

The starting material SOD is the product obtained by extraction from its sources, namely living organisms such as animals (human, bovine, etc.), plants and microorganisms by a known method, or obtained by using genetic engineering techniques. The chemical structure (with respect to coordinated metal, molecular weight, amino acid sequence, etc.) of SOD has been elucidated to a considerable extent. SOD species are now classified into three groups, that is, Fe—SOD, Mn—SOD and Cu·Zn—SOD and have a molecular weight of 30,000 to 80,000 which depends on the living organisms and the place where they are present. The amino acid sequences of the three SOD species also differ from each other to some extent [yoshihiko Ohyanagi, "SOD to Kasseisanso Chosetsuzai (SOD and Superoxide Controlling Agent)", Chapter 2 "SOD", published by Nihon Igakukan on Nov. 6, 1989]. Human-type Cu·Zn—SOD has a molecular weight of 32,000 and two reactive mercapto groups. This human-type SOD can be obtained, for example, by subjecting the human blood to heat treatment, ion-exchange chromatography and gel filtration in this order, or by using genetic engineering techniques.

The long chain carboxylic acid maleimide (II) can be synthesized by the reaction of an aminocarboxylic acid (hereinafter referred to as "aminocarboxylic acid (III)") represented by the following general formula $$H_2N-W-CO_2H \quad (III)$$

wherein W is as defined above, with maleic anhydride to produce an amidodicarboxylic acid (hereinafter referred to as "amidodicarboxylic acid (IV)") represented by the following general formula

$$(IV)$$

wherein W is as defined above, and the ring closure of the thus obtained amidodicarboxylic acid (IV) by a per se known method [Organic Synthesis, 41, 93 (1961) and "Shin Jikken Kagaku Koza, 14–II" 1145-1147, published by Maruzen in 1978]. Further, the long chain carboxylic acid maleimide (II) can also be synthesized by partially modified procedures of this method.

For the synthesis of the aminocarboxylic acid (III), the use of a per se known process applying Gabriel's method [Ber., 22, 426 (1889)] for the synthesis of an amino acid as the key reaction is simple and easy. That is, a hydroxycarboxylic acid ester (hereinafter referred to as "hydroxycarboxylic acid ester (V)") represented by the following general formula $$HO-W-CO_2R^1 \quad (V)$$

wherein W is as defined above and $R^1$ is a lower alkyl group, is treated with a sulfonyl halide such as p-toluenesulfonyl chloride or methanesulfonyl chloride to give its sulfonic acid ester (hereinafter referred to as "sulfonic acid ester (VI)") represented by the following general formula (VI)

$$(VI)$$

Wherein W and $R^1$ are as defined above and $R^2$ represents a lower alkyl group or an aryl group which may be substituted with a lower alkyl group. The thus obtained sulfonic acid ester (VI) is converted to phthalimide carboxylic acid ester (hereinafter referred to as "phthalimide carboxylic acid ester (VII)") represented by the following general formula

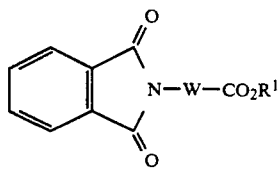

(VII)

wherein W and $R^1$ are as defined above, by reaction with a phthalimide alkaline metal salt according to Gabriel's method. The obtained phthalimide carboxylic acid ester (VII) is treated with hydrazine to allow its phthalimide group to decompose, to give an aminocarboxylic acid ester, which is then hydrolyzed under alkaline condition to produce the aminocarboxylic acid (III). The reaction of the hydroxycarboxylic acid ester (V) with sulfonic acid halide is conducted usually in the presence of a base, such as pyridine or triethylamine, and in the presence or absence of a suitable solvent, such as methylene chloride or ether, at a temperature in a range of $-20°$ to $+50°$ C.

The reaction of the sulfonic acid ester (VI) with a phthalimide alkali metal salt is generally carried out in the presence or absence of a polar solvent having a high boiling point, conveniently in the presence of N,N-dimethylformamide. That is, phthalimide potassium salt is dissolved in N,N-dimethylformamide, and to the obtained solution the sulfonic acid ester (VI) is added at a temperature in a range of room temperature to $153°$ C., preferably in a range of $80°$ to $120°$ C.

The conversion of the thus obtained phthalimide carboxylic acid ester (VII) to the aminocarboxylic acid (III) is carried out by treating the phthalimide carboxylic acid ester (VII) with hydrazine to decompose the phthalimide group, and then hydrolyzing under an alkaline condition the aminocarboxylic acid ester that formed. That is, the phthalimide carboxylic acid ester is dissolved in a suitable solvent, such as ethanol or methanol, hydrazine is added to the solution obtained, and the mixture is stirred. After removal of the phthalhydrazide that formed, the remaining aminocarboxylic acid ester is, according to a known method, stirred in a solution of sodium hydroxide or potassium hydroxide in an aqueous methanol, ethanol or isopropanol. Hydrazine is used preferably in an amount of about 1.0 to 20 moles, more preferably 1.0 to 10 moles, per mole of the phthalimide carboxylic acid ester (VII). For smooth proceeding of the reaction, the reaction temperature is preferably in a range of $0°$ C. to the boiling point of the solvent used, more preferably in a range of $25°$ C. to the boiling point. The reaction period is, while depending on the temperature employed, usually in a range of 10 minutes to 3 days.

The phthalhydrazide that forms by the above reaction is, readily and conveniently, removed by acidifying the reaction mixture with a mineral acid, e.g. hydrochloric acid and sulfuric acid, at a temperature under ice-cooling to cause it to precipitate, and then filtering off the precipitate. After this procedure the solvent is distilled off and the residue aminocarboxylic acid ester is hydrolyzed under an alkaline condition. It is desirable to conduct the hydrolysis at a temperature in a range of from $0°$ C. to the boiling point of the solvent, more preferably in a range of from $25°$ C. to the boiling point. The time required for the completion of the hydrolysis is, depending on the temperature employed, generally in a range of from 10 minutes to 3 days. After the completion of the hydrolysis, the aminocarboxylic acid (III) is isolated from the reaction mixture by, suitably, neutralizing it with a mineral acid, e.g. hydrochloric acid and sulfuric acid, at a temperature in a range of from room temperature to ice-cooled temperature to form precipitates, and collecting the precipitates by filtration, followed by recrystallization thereof.

The reaction of the aminocarboxylic acid (III) with maleic anhydride is desirably carried out in a solvent. Examples of preferred solvents are aqueous alcohols such as aqueous methanol, aqueous ethanol and aqueous isopropanol. For smooth proceeding of the reaction, the pH of the reaction mixture is preferably maintained at at least 6. If the pH is lower than 6, the solubility of the aminocarboxylic acid (III) will decrease, whereby the reaction hardly proceeds. Maleic anhydride is used generally in an amount of 1 to 300 moles, preferably 1 to 50 moles per mole of the aminocarboxylic acid (III). In a preferred embodiment, maleic anhydride is added all at once or gradually added in portions to a solution or dispersion of the aminocarboxylic acid (III) and the mixture is stirred. The reaction temperature is preferably in a range of from $0°$ C. to the boiling point of the solvent, more preferably in a range of from $20°$ to $60°$ C. The proceeding of the reaction is conveniently checked by monitoring the consumption of the starting material by thin layer chromatography. After the completion of the reaction, the amidodicarboxylic acid (IV) that formed is isolated from the reaction mixture by, suitably, acidifying the mixture to a pH of about 1 to 4 with a mineral acid, e.g. hydrochloric acid and sulfuric acid, at a temperature in a range of from room temperature to ice-cooled temperature to form precipitates, and collecting the precipitates by filtration, followed by recrystallization thereof.

The amidodicarboxylic acid (IV) can readily be converted to the long chain carboxylic acid maleimide (II) by a conventional method, for example by heating it together with acetic anhydride in the presence of sodium acetate.

The long chain carboxylic acid maleimide (II) has a fatty acid portion. The SOD derivative comprising such long chain carboxylic acid maleimide (II) therefore is capable of reversibly binding plasma protein and biomembrane, whereby it has prolonged plasma half-life and good delivery property to organs.

It is preferable that, in the long chain carboxylic acid maleimide (II), the long chain hydrocarbon residue represented by W have 9 to 29, more preferably 17 to 23 principal chain atoms. If a long chain carboxylic acid maleimide (II) with the number of principal chain atoms being less than 9 is reacted with SOD, the resulting SOD derivative will have poor affinity to plasma protein. If the number is larger than 29, the long chain carboxylic acid maleimide (II) will have poor solubility in an aqueous solution with a pH of 6 to 10, whereby it becomes difficult to bond such long chain carboxylic acid maleimide (II) to the SOD.

The SOD derivative has, as is apparent from the results obtained in Test Examples 2 and 3 which will be described later herein, excellent anti-ulcer and anti-arrhythmic activities, and also has pharmacological activities such as anti-inflammatory, anti-ischemic and cerebral edemapreventing activities.

Toxicological studies have shown the low toxicity of the SOD derivative of the present invention.

The above results show that the SOD derivatives of the present invention are effective for treating various diseases caused by active oxygen species, and can be used as anti-inflammatory agents, anti-ulcer agents, anti-ischemic agents, cerebral edema-preventing agents, anti-paraquat intoxication agents, etc. and are also useful as drugs to alleviate various side effects induced by anti-cancer agents, as caused by active oxygen species. Further, the SOD derivatives are useful as therapeutic agents for treating dermal diseases such as burn, trauma, various dermatides, etc.

The SOD derivatives of the present invention more effectively retain the pharmacological activities inherent to unmodified SOD [Saishin Igaku, 39, No. 2, 339 (1984); Igaku to yakugaku, 14No. 1, 55 (1985); Jikken Igaku, 4, No. 1 (1986) "Tokushuh: Seitainai Furii Rajikaru to Shikkan" (Special Number: Free Radicals and Diseases); Fragrance Journal, 79, 89 (1986)]. Moreover, the SOD derivatives of the present invention have pharmacological activities against those diseases caused by active oxygen species and those against which unmodified SOD shows no pharmacological activities.

The dosage of the SOD derivative depends on the kind of disease, severity of the disease, patient's tolerance and other factors. However, the usual daily dosage for adult humans is 0.1 to 500 mg and preferably 0.5 to 100 mg, either in a single dose or in a few divided doses. The SOD derivative may be provided in various dosage forms suitable for the respective routes of administration.

Thus, the SOD derivative can be formulated and prepared by the established pharmaceutical procedures. Therefore, the present invention covers a variety of pharmaceutical compositions containing at least one species of the SOD derivative as an active ingredient. Such pharmaceutical compositions can be manufactured using pharmaceutically acceptable carriers, vehicles and other auxiliary substances which are commonly used in pharmaceutical practice.

When such pharmaceutical compositions are intended for oral administration, they are preferably provided in dosage forms suitable for absorption from the gastrointestinal tract. Tablets and capsules which are unit dosage forms for oral administration may contain binders such as syrup, gum arabic, gelatin, sorbitol, gum tragacanth and polyvinylpyrrolidone; excipients such as lactose, corn starch, calcium phosphate, sorbitol and glycine; lubricants such as magnesium stearate, talc, polyethylene glycol and silica; disintegrators such as potato starch; pharmaceutically acceptable wetting agents such as sodium laurylsulfate and so on. The tablets may be coated in the well-known manner. Liquid preparations for oral administration may be aqueous or oily suspensions, solutions, syrups, elixirs and so on, or may be lyophilisates which are extemporaneously reconstituted with water or other suitable vehicles before use. Such liquid preparations may contain the usual additives inclusive of suspending agents such as sorbitol syrup, methylcellulose, glucose/sucrose syrup, gelatin, hydroxyethylcellulose, carboxymethylcellulose, aluminum stearate gel and hydrogenated edible oils and fats; emulsifiers such as lecithin, sorbitan monooleate and gum arabic; non-aqueous vehicles such as almond oil, fractionated coconut oil, oleaginous esters, propylene glycol and ethanol; preservatives such as methyl p-hydroxybenzoate, propyl p-hydroxybenzoate and sorbic acid; and so forth.

For preparing injections, the SOD derivative is dissolved in an suitable solvent such as physiological saline and glucose solution for injection; and the SOD derivative concentration is adjusted to 2 to 20 mg per 2 to 10 ml of solvent in a conventional manner to give injections for subcutaneous, intramuscular or intravenous administration. In preparing the above injections, pH-adjusting agents, buffers, stabilizers, preservatives, solubilizers and so forth may be added to the aqueous solution, if necessary.

The above-mentioned pharmaceutical composition can contain the SOD derivative in a concentration selected according to the form thereof and other factors, generally in a concentration of about 0.01 to 50% by weight, preferably about 0.1 to 20% by weight.

EXAMPLES

Other features of the invention will become apparent in the course of the following descriptions of exemplary embodiments which are given for illustration of the invention and are not intended to be limiting thereof.

$^1$H—NMR is measured using tetramethylsilane as internal standard. IR absorption spectrum is measured by KBr disk method.

REFERENCE EXAMPLE 1

Synthesis of methyl 18-tosyloxyoctadecanoate

In 50 ml of methylene chloride, methyl 18-hydroxyoctadecanoate (4.5 g, 14.3 mmoles) was dissolved. To the obtained solution was added pyridine (4.53 g, 57.2 mmoles), and then was gradually added p-toluenesulfonyl chloride (5.46 g, 28.6 mmoles) with ice-cooling over a period of 1 hour. Thereafter, reaction was carried out for 16 hours in a refrigerator. The reaction mixture was washed with a 10% aqueous hydrochloric acid solution, water, saturated aqueous sodium hydrogen carbonate solution, water and aqueous sodium chloride solution in this order, dried, and then concentrated under reduced pressure. The residue was isolated and purified by silica gel column chromatography (eluent: benzene) to give methyl 18-tosyloxyoctadecanoate (5.69 g, 85%) having the following properties.

m.p. 67.5°–68.5° C.

$^1$H—NMR (CDCl$_3$, 270 MHz): δ1.09–1.42 (m, 26H), 1.53–1.72 (m, 4H), 2.30 (t,2H), 2.45 (s, 3H), 3.68 (s, 3H), 4.03 (t, 2H), 7.35 (d, 2H), 7.79 (d, 2H)

REFERENCE EXAMPLE 2

Synthesis of methyl 18-phthalimidooctadecanoate

A mixture of potassium phthalimide (2.96 g, 16.0 mmoles) and 100 ml of dried N,N-dimethylformamide was heated at 110° C. To this mixture was added dropwise 80 ml of a solution of methyl 18 tosyloxyoctadecanoate (5.0 g, 10.7 mmoles) in 80 ml of N,N-dimethylformamide, and the mixture was heated with stirring at 110° C. for 2 hours. The reaction mixture was poured into ice water to a total volume of 1.2 l, and stirred for 30 minutes. Thereafter, the precipitates that formed were collected by filtration and dissolved in chloroform. The obtained solution was washed with water and then with saturated aqueous sodium chloride solution, dried over anhydrous magnesium sulfate, and isolated and purified by silica 9el column chromatography [eluent: mixture of benzene and methylene chloride (volume ratio: 2:1)], to give methyl 18-phtahlimideocatadecanoate (4.15 g, 88%) having the following properties.

m.p. 82°–83° C.

¹H—NMR (CDCl₃, 270 MHz): δ1.09-1.42 (m, 26H), 1.53-1.76 (m, 4H), 2.30 (t,2H), 3.66, 3.67 (s, t, 5H), 7.71 (m, 2H), 7.84 (m, 2H)

REFERENCE EXAMPLE 3

Synthesis of 18-aminooctadeoanoic acid

A mixture of methyl 18-phthalimideoctadecanoate (2.0 g, 4.51 mmoles), 30 ml of ethanol and 80% hydrazine hydrate (0.42 ml, 6.76 mmoles) was refluxed for 9 hours. To the reaction mixture was added 6N aqueous hydrochloric acid solution (11.3 ml, 67.6 mmoles) and the resulting mixture was refluxed for 1 hour. The insoluble matter that formed was filtered off, and the filtrate was concentrated under reduced pressure. To the residue were added 30 ml of ethanol and 18.1 ml of 1N aqueous sodium hydroxide solution, and the mixture was refluxed for 18 hours. The reaction mixture was neutralized with 6N aqueous hydrochloric acid solution under ice-cooled condition. The precipitates that formed were collected by filtration and recrystallized from ethanol-acetic acid-water to give 18-aminooctadecanoic acid (800 mg, 59%) having the following properties.

m.p. 172°-174° C.
IR (cm⁻¹): 2920, 2850, 1640, 1535, 1470, 1400
FD-MS (m/z): [M+H]⁺300

REFERENCE EXAMPLE 4

Synthesis of N-(17-carboxyheptadecyl)maleamic acid

In a mixture of 50 ml of ethanol and 25 ml of 1N aqueous sodium hydroxide solution, 18-aminooctadecanoic acid (400 mg, 1.33 mmoles) was dissolved at 40° C. To the obtained solution, being maintained at 40° C., was gradually added maleic anhydride (1.97 g, 20.0 mmoles) over a period of 2 hours. The reaction mixture was stirred for 30 minutes, then acidified with hydrochloric acid under ice-cooled condition and subjected to centrifugation. The precipitate was collected by filtration, sufficiently washed with water and then dried under reduced pressure, to give N-(17-carboxyheptadecyl)maleamic acid (436 mg, 88%) having the following properties.

m.p. 144°-147.5° C.
IR (cm⁻¹): 3305, 2920, 2850, 1710, 1630, 1585, 1470, 1400, 1280, 1250, 1230, 1215, 1195, 1180
FD-MS(m/z): [M+H]⁺398

EXAMPLE 1

Synthesis of 18-maleimidooctadecanoic acid

A mixture of N-(17-carboxyheptadecyl)maleamic acid (400 mg, 1.01 mmoles), 2.83 ml of acetic anhydride, and anhydrous sodium acetate (41.0 mg, 0.50 mmoles) was heated at 100° C. with stirring for 1 hour. The reaction mixture was allowed to cool, then poured onto ice and stirred for 1 hour. The resulting mixture was extracted with chloroform. The separated organic layer was washed with water and then with saturated aqueous sodium chloride solution, dried over anhydrous magnesium sulfate, concentrated under reduced pressure and isolated and purified by silica gel column chromatography [eluent: mixture of benzene and chloroform (volume ratio: 1:1)], to give 18-maleimidooctadecanoic acid (172 mg, 45%) having the following properties.

m.p. 101°-103° C.

¹H—NMR(CDCl₃, 270 MHz): δ1.14-1.40 (m, 26H), 1.48-1.72 (m, 4H), 2.35 (t,2H), 3.50 (t, 2H), 6.68 (s, 2H)
IR(cm⁻¹): 2920, 2850, 1710, 1470, 1450, 1410, 840, 700
FD-MS (m/z): [M⁺+H]⁺380

REFERENCE EXAMPLE 5

Synthesis of methyl 20-tosyloxyeicosanoate

In 90 ml of methylene chloride was dissolved methyl 20-hydroxyeicosanoate (8.0 g, 23.4 mmoles). To the obtained solution were added pyridine (7.93 g, 93.4 mmoles) and then, under ice-cooling, p-toluenesulfonyl chloride (8.90 g, 46.7 mmoles) gradually over a period of 1 hour. The mixture was stirred for 14 hours in a refrigerator. After the completion of the reaction, the reaction mixture was subjected to the same after-treatment steps as in Reference Example 1, to give methyl 20-tosyleicosanoate (10.57 g, 91%) having the following properties.

m.p. 72.5°-73.5° C.
¹H—NMR (CDCl₃, 270 MHz): δ1.10-1.38 (m, 30H), 1.52-1.72 (m, 4H), 2.30 (t, 2H), 2.45 (s, 3H), 3.67 (s, 3H), 4.02 (t, 2H), 7.34 (d, 2H), 7.78 (d, 2H)

REFERENCE EXAMPLE 6

Synthesis of methyl 20-phtalimidoeicosanoate

A mixture of potassium phthalimide (5.59 g, 30.2 mmoles) and 200 ml of dried N,N-dimethylformamide was heated to 110° C. To this mixture was added dropwise methyl 20-tosyloxyeicosanoate (10.0 g, 20.1 mmoles) dissolved in 300 ml of N,N-dimethylformamide and the resulting mixture was heated at 110° C. with stirring for 2 hours. After the completion of the reaction, the reaction mixture was treated in the same manner as in Reference Example 2 to give methyl 20-phthalimidoeicosanoate (8.97 g, 95%) having the following properties.

m.p. 86.5°-87.5° C.
¹H—NMR (CDCl₃, 270 MHz): δ1.08-1.50 (m, 30H), 1 55-1.81 (m, 4H), 2.30 (t, 2H), 3.66, 3.67 (s, t, 5H), 7.71 (m, 2H), 7.84(m, 2H)

REFERENCE EXAMPLE 7

Synthesis of 20-aminoeicosanoic acid

A mixture of methyl 20-phthalimidoeicosanoate (5.0 g, 10.6 mmoles), 100 ml of ethanol, 80% hydrazine hydrate (1.0 ml, 15.9 mmoles) was refluxed for 9 hours. After the addition of 26.5 ml of 6N aqueous hydrochloric acid, the reaction mixture was further refluxed for 1 hour. The insoluble matter that formed was removed by filtration. The filtrate was concentrated under reduced pressure. To the residue were added 70 ml of ethanol and 42.4 ml of 1N aqueous sodium hydroxide solution, and the obtained reaction mixture was refluxed for 16 hours. The reaction mixture was neutralized by adding 6N aqueous hydrochloric acid solution under ice-cooled condition. The precipitates that formed were collected by filtration and recrystallized from ethanolacetic acid-water, to give 20-aminoeicosanoic acid (2.50 g, 72%) having the following properties.

m.p. 172.5°-174° C.
FD-MS (m/z): [M+H]⁺328

REFERENCE EXAMPLE 8

Synthesis of N-(19-carboxynonadecyl)maleamic acid

In a mixture of 85 ml of ethanol and 40 ml of 1N aqueous sodium hydroxide solution, 20-aminoeicosanoic acid (500 mg, 1.53 mmoles) was dissolved at 40° C. To the obtained solution, while maintained at 40° C., was gradually added maleic anhydride (3.75 g, 38.3 mmoles) over a period of 3 hours. The pH of the reaction mixture was kept at 8–10 during the addition. The reaction mixture was stirred for 30 minutes and then treated in the same manner as in Reference Example 4, to give N-(19-carboxynonadecyl)maleamic acid (538 mg, 83%) having the following properties.

m.p. 146°–148° C.
FD-MS (m/z): [M+H]+426
IR (cm$^{-1}$): 3305, 2920, 2850, 1710, 1630, 1570, 1470, 1405, 1275, 1245, 1225, 1210, 1195, 1180

EXAMPLE 2

Synthesis of 20-maleimidoeicosanoic acid

A mixture of N-(19-carboxynonadecyl)maleamic acid (500 mg, 1.22 mmoles), 3.44 ml of acetic anhydride and anhydrous sodium acetate (50.1 mg, 0.61 mmole) was reacted for 1 hour at 100° C. After the completion of reaction, the reaction mixture was treated in the same manner as in Example 1, to give 20-maleimidoeicosanoic acid (230 mg, 46%) having the following properties.

m.p. 104°–105.5° C.
$^1$H—NMR (CDCl$_3$, 270 MHz): δ1.17–1.40 (m, 30H), 1.50–1.69 (m, 4H), 2.34 (t, 2H), 3.51 (t, 2H), 6.68 (s, 2H)
FD-MS (m/z): [M+D]+408
IR (cm$^{-1}$): 2920, 2850, 1710, 1470, 1455, 1410, 840, 700

REFERENCE EXAMPLE 9

Synthesis of methyl 22-tosyloxydocosanoate

In a mixed solvent of 15 ml pyridine and 120 ml of methylene chloride was dissolved methyl 22-hydroxydocosanoate (1.70 g, 4.59 mmoles). p-toluenesulfonyl chloride (1.75 g, 9.18 mmoles) was gradually added to the obtained solution under ice-cooled condition, over a period of 1 hour, and the mixture was stirred for 14 hours in a refrigerator. Then, p-toluenesulfonyl chloride (1.75 g, 9.18 mmoles) was added to the reaction mixture, and reaction was effected for 24 hours. After the completion of reaction, the reaction mixture was treated in the same manner as in Reference Example 1, to give methyl 22-tosyloxydocosanoate (2.28 g, 75%) having the following properties.

m.p. 74°–76° C.
$^1$H—NMR (CDCl$_3$, 270 MHz): δ1.08–1.40 (m, 34H), 1.53–1.72 (m, 4H), 2.30 (t, 2H), 2.45 (s, 3H), 3.67 (s, 3H), 4.02 (t, 2H), 7.35 (d, 2H), 7.80 (d, 2H)

REFERENCE EXAMPLE 10

Synthesis of methyl 22-phthalimidodocosanoate

A mixture of potassium phthalimide (1.16 g, 6.29 mmoles) and 40 ml of dried N,N-dimethylformamide was heated up to 110° C. To this mixture was added dropwise a solution of methyl 22-tosyloxydocosanoate (2.20 g, 4.19 mmoles) in 70 ml of N,N-dimethylformamide, and the reaction mixture was reacted for 2 hours at 110° C. After the completion of reaction, the reaction mixture was subjected to the same after-treatment steps as in Reference Example 2, to give methyl 22-phthalimidodocosanoate (1.57 g, 95%) having the following properties.

m.p. 88.5°–90.5° C.
$^1$H—NMR (CDCl$_3$, 270 MHz): δ1.12–1.41 (m, 34H), 1.54–1.75 (m, 4H), 2.30 (t, 2H), 3.66, 3.67 (s, t, 5H), 7.71 (m, 2H), 7.84 (m, 2H)

REFERENCE EXAMPLE 11

Synthesis of 22-aminodocosanoic acid

A mixture of methyl 22-phthalimidodocosanoate (1.5 g, 3.0 mmoles), 40 ml of ethanol and 80% hydrazine hydrate was refluxed for 10 hours. To the reaction mixture was added 11.3 ml of 6N aqueous hydrochloric acid solution, and further refluxed for 1 hour. After removal by filtration of the insoluble matter that formed, the reaction mixture was concentrated under reduced pressure. To the residue were added 30 ml of ethanol and 15 ml of 1N aqueous sodium hydroxide solution, and the resulting mixture was refluxed for 19 hours. After neutralization of the reaction mixture with 6N aqueous hydrochloric acid solution, the precipitates that formed were collected by filtration and recrystalized from ethanol-acetic acid-water to give 22-aminodocosanoic acid (827 mg, 77%) having the following properties.

m.p. 166°–168° C.
FD-MS (m/z): [M+H]+356
IR (cm$^{-1}$): 2920, 2850, 1640, 1535, 1470, 1400

REFERENCE EXAMPLE 12

Synthesis of N-(21-carboxyheneicosyl)maleamic acid

In a mixture of 100 ml of ethanol and 50 ml of 1N aqueous sodium hydroxide solution, 22-aminodocosanoic acid (400 mg, 1.12 mmoles) was dissolved at 40° C. To the obtained solution, the temperature being maintained at 40° C., maleic anhydride (4.39 g, 44.8 mmoles) was gradually added over a period of 5 hours. The reaction mixture was kept at a pH of 8–10 during the addition, and the mixture was stirred for additional 30 minutes and then treated in the same manner as in Reference Example 4, to give N-(21-caboxyheneicosyl)maleamic acid (538 mg, 83%) having the following properties.

m.p. 140°–143° C.
FD-MS (m/z): [M+H]+454
IR (cm$^{-1}$): 3305, 2920, 2850, 1710, 1630, 1570, 1470, 1275, 1245, 1225, 1210, 1195, 1180

EXAMPLE 3

Synthesis of 22-maleimidodocosanoic acid

A mixture of N-(21-carboxyheneicosyl)maleamic acid (450 mg, 0.99 mmoles), 2.8 ml of acetic anhydride, and anhydrous sodium acetate (40.7 mg, 0.50 mmoles) was reacted at 100° C. for 1 hour. After the completion of reaction, the reaction mixture was treated in the same manner as in Example 1, to give 22-maleimidodocosanoic acid having the following properties.

m.p. 105.5°–106.5° C.
$^1$H—NMR (CDCl$_3$, 270 MHz): δ1.12–1.42 (m, 34H), 1.50–1.71 (m, 4H), 2.34 (t, 2H), 3.51 (t, 2H), 6.68 (s, 2H)
FD-MS (m/z): [M+H]+436
IR (cm$^{-1}$): 2920, 2850, 1710, 1475, 1450, 1415, 840, 700

EXAMPLE 4

Preliminary Experiment for the Synthesis of an SOD Derivative by the Reaction of 18-maleimidooctadecanoic Acid with SOD Seven same solution samples were prepared by dissolving human-type SOD (1 mg, 31 nmoles) in 0.91 ml of 0.1M tris(hydroxymethyl)aminomethane-hydrochloric acid buffer (pH 9). Amounts described in the following Table 1 of the 18-maleimidooctadecanoic acid obtained in Example 1 were each dissolved in 0.1 ml of dimethyl sulfoxide and the obtained solutions were each added to the above samples of SOD solution with stirring. After an additional stirring for 2 days in a refrigerator, the reaction mixtures were subjected to electrophoresis. The schematic electrophorograms are shown in FIG. 1. In FIG. 1, (a), (b), (c), (d), (e), (f), and (g) show electrophorograms of reaction mixtures which were obtained with the mole ratio of 18-maleimidooctadecanoic acid to SOD being 0, 1, 2, 5, 10, 20 and 50, respectively.

TABLE 1

| No. | Mole ratio | Weight (mg) |
| --- | --- | --- |
| 1 | 0 | 0 |
| 2 | 1 | 0.12 |
| 3 | 2 | 0.24 |
| 4 | 5 | 0.47 |
| 5 | 10 | 1.19 |
| 6 | 20 | 2.37 |
| 7 | 50 | 5.93 |

In Table 1, "Mole ratio" represents the mole ratio of 18-maleimidooctadecanoic acid to SOD, and "Weight" represents that of 18-maleimidooctadecanoic acid.

As shown in FIG. 1, the products obtained by the reactions with the mole ratio of 18-maleimidooctadecanoic acid to SOD being 2 or more are all nearly same, which shows that all the reactive functional groups in SOD have completely reacted in these reactions.

In FIG. 1, bands (1), (2) and (3) correspond to the charge isomers of the SOD's used for the above preliminary experiment respectively. Bands (4), (5) and (6) correspond to SOD derivatives comprising the charge isomers corresponding to bands (1), (2) and (3), respectively, to each of which one molecule of 18-maleimidooctadecanoic acid is bonded. Bands (7), (8) and (9) correspond to SOD derivatives comprising the charge isomers corresponding to bands (1), (2) and (3), respectively, to each of which 2 molecules of 18-maleimidooctadecanoic acid are bonded.

Synthesis of an SOD Derivative by the Reaction of SOD with 18-maleimidooctadecanoic Acid To 1.12 ml of human-type SOD (88.95 mg/ml) were added 1.68 ml of water and 0.8 ml of 0.5M tris(hydroxymethyl)aminomethane-hydrochloric acid buffer (pH 9). Then, a solution prepared by dissolving 4.7 mg of the 18-maleimidooctadecanoic acid obtained in Example 1 was gradually added with stirring, and the reaction mixture was stirred overnight at room temperature. The reaction mixture was filtered and the filtrate was subjected to gel filtration using a column packed with Sephadex G-25 (trademark; Pharmacia Fine Chemicals) (eluent: 10 mM aqueous ammonium hydrogen carbonate solution) and the high-molecular-weight fractions were collected. The obtained fractions as such were subjected to ion-exchange chromatography using DEAE-Sepharose Fast Flow (trademark; Pharmacia Fine Chemicals) (eluent: a mixture of 10 mM Tris-hydrochloric acid butter (pH 8) and 0.075M aqueous sodium chloride solution), and the fractions containing the resulting SOD derivative were collected. The collected fractions were subjected to gel filtration by using a column packed with Sephadex G-25 (eluent: 10 mM aqueous ammonium hydrogen carbonate solution), desalinized and the high-molecular-weight fractions were combined and lyophilized to give 52 mg of the SOD derivative. From the obtained SOD derivative no free SH group was detected.

Figure 2:
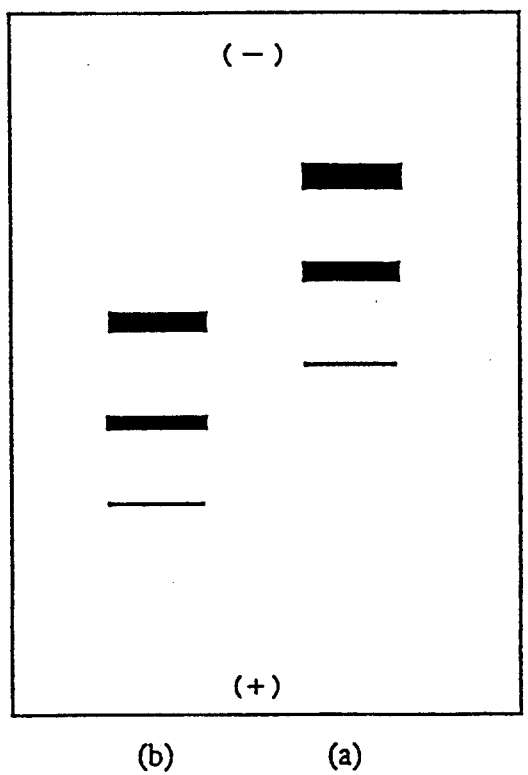
FIG. 2 shows schematic electrophorograms of (a) SOD used in Example 4 and (b) SOD derivative obtained in Example 4.
Figure 3:
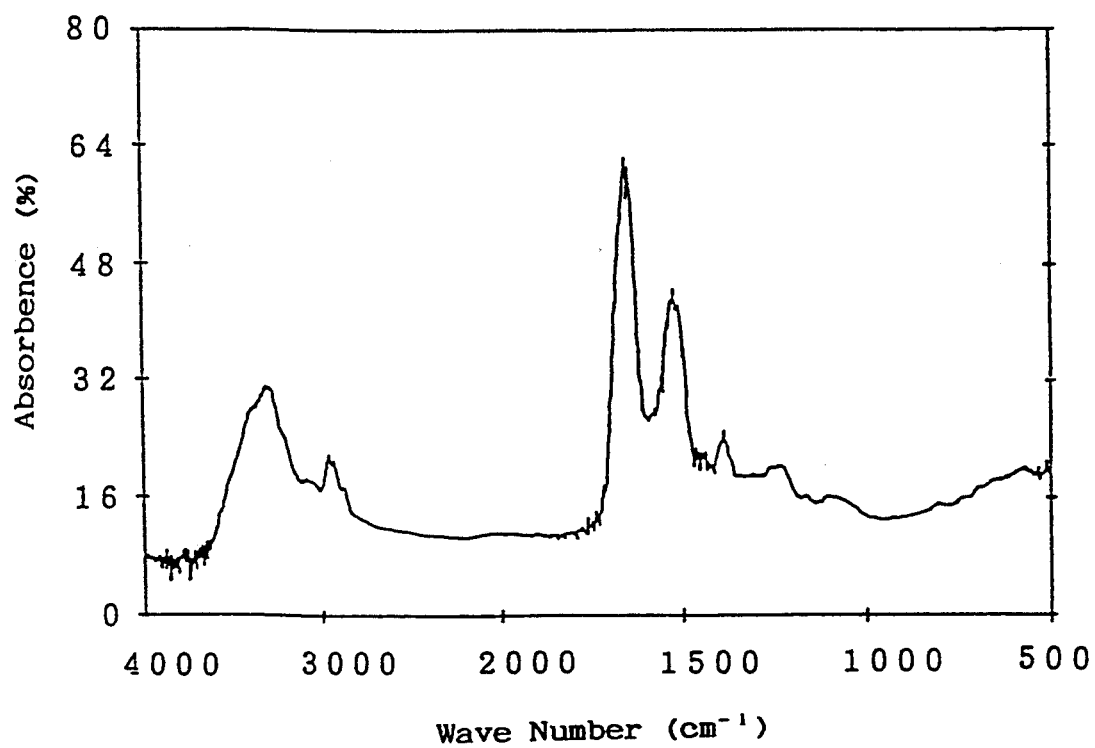
FIG. 3 shows an IR-spectrum of the SOD derivative obtained in Example 4.

The schematic electrophorograms of the SOD used and the SOD derivative obtained are shown in FIG. 2 (a) and (b). Bands in FIG. 2 (b) were identical with bands (7), (8) and (9) in FIG. 1 respectively. From this fact and the quantitative determination result of SH group, the obtained SOD derivative was identified to be that comprising SOD with its 2 SH groups each bonded to 1 molecule of 18-maleimidooctadecanoic acid. FIG. 3 shows an IR spectrum of the SOD derivative.

EXAMPLE 5

Synthesis of an SOD Derivative by the Reaction of SOD with 20-maleimidoeicosanoic Acid To 1.12 ml of human-type SOD (88.95 mg/ml) were added 1.68 ml of water and 0.8 ml of 0.5M aqueous tris(hydroxymethyl)aminomethane solution. Then, a solution prepared by dissolving 5.1 mg of the 20-maleimidoeicosanoic acid obtained in Example 2 was gradually added with stirring, and the mixture was stirred overnight at room temperature. The reaction mixture was filtered, and the filtrate was subjected to gel filtration using a column packed with Sephadex G-25 (eluent: 10 mM aqueous ammonium hydrogen carbonate solution) and the high-molecular-weight fractions were collected. The obtained fractions as such were subjected to ion-exchange chromatography using DEAE-Sepharose Fast Flow (eluent: a mixture of 10 mM Tris-hydrochloric acid butter (pH 8) and 0.10M aqueous sodium chloride solution), and the fractions containing the resulting SOD derivative were separated. The obtained fractions were subjected to gel filtration by using a column packed with Sephadex G-25 (eluent: 10 mM aqueous ammonium hydrogen carbonate solution), desalinized and the high-molecular-weight fractions were combined and lyophilized to give 33 mg of the SOD derivative. From the obtained SOD derivative no free SH group was detected.

Figure 4:
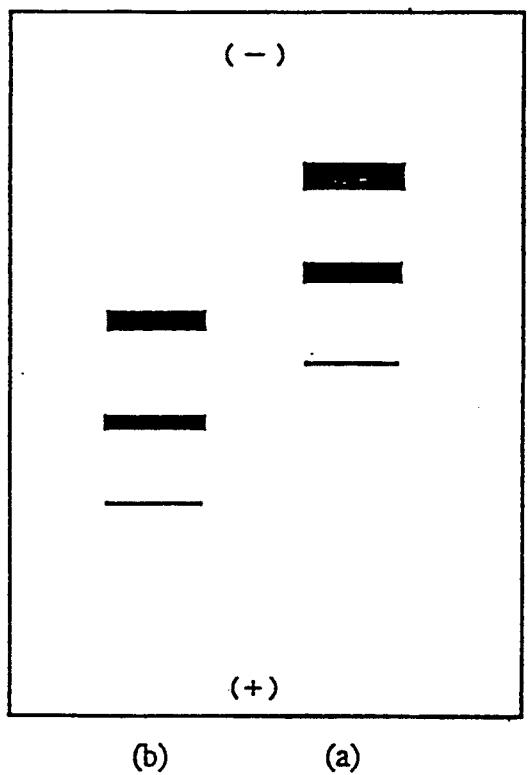
FIG. 4 shows schematic electrophorograms of (a) the SOD used in Example 5 and (b) the SOD derivative obtained in Example 5.
Figure 5:
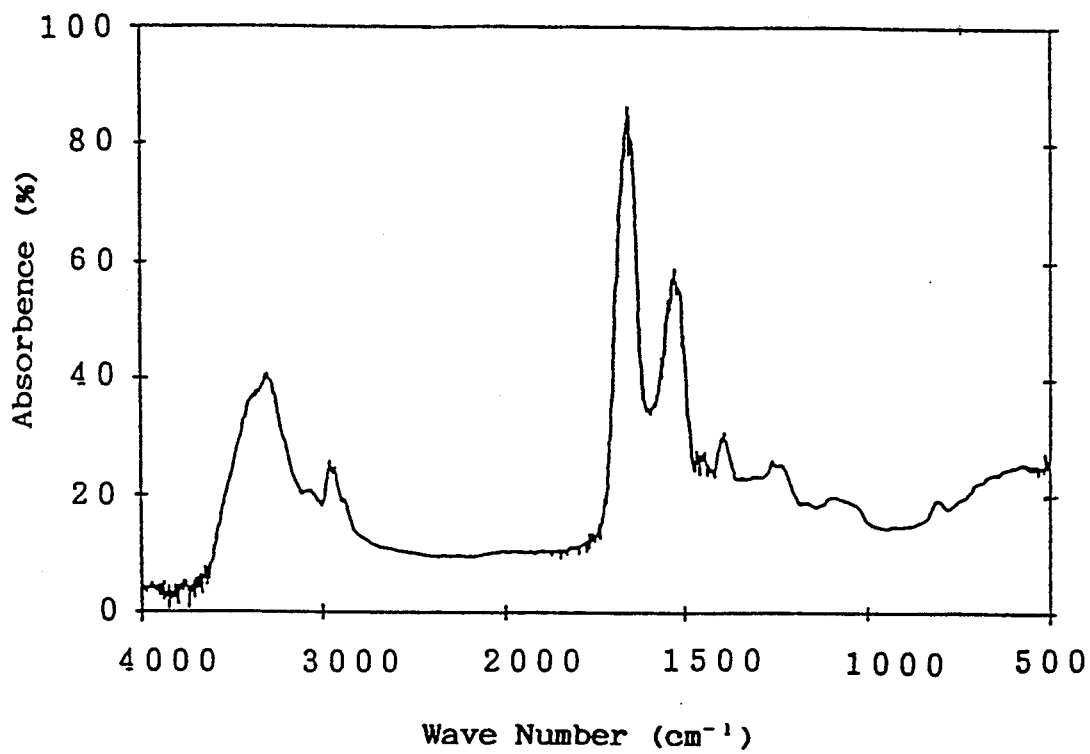
FIG. 5 shows an IR-spectrum of the SOD derivative obtained in Example 5.

The schematic electrophorograms of the SOD used and the SOD derivative obtained are shown in FIG. 4 (a) and (b). The obtained SOD derivative was identified, in the same manner as in Example 4, to be that comprising SOD with its 2 SH groups each bonded to 1 molecule of 20-maleimidoeicosanoic acid. FIG. 5 shows an IR spectrum of the SOD derivative.

EXAMPLE 6

Synthesis of an SOD Derivative by the Reaction of SOD with 22-maleimidodocosanoic Acid To 1.12 ml of human-type SOD (88.95 mg/ml) were added 4.88 ml of water and 4.0 ml of 0.5M tris(hydroxymethyl)aminomethane-hydrochloric acid buffer (pH 9). Then, a solution prepared by dissolving 5.1 mg of the 20-maleimidoeicosanoic acid obtained in Example 3 was gradually added with stirring, and the mixture was stirred overnight at room temperature. The reaction mixture was filtered, and the filtrate was subjected to gel filtration using a column packed with Sephadex G-25 (eluent: 10 mM aqueous ammonium hydrogen carbonate solution) and the high-molecular-weight fractions were collected. The obtained fractions as such were subjected to ion-exchange chromatography using DEAE-Sepharose Fast Flow (eluent: a mixture of 10 mM Trishydrochloric acid butter (pH 8) and 0.15M aqueous sodium chloride solution), and the fractions containing the resulting SOD derivative were separated. The separated fractions were subjected to gel filtration by using a column packed with Sephadex G-25 (eluent: 10 mM aqueous ammonium hydrogen carbonate solution), desalinized and the high-molecular-weight fractions were combined and lyophilized to give 42 mg of the SOD derivative. From the obtained SOD derivative no free SH group was detected.

Figure 6:
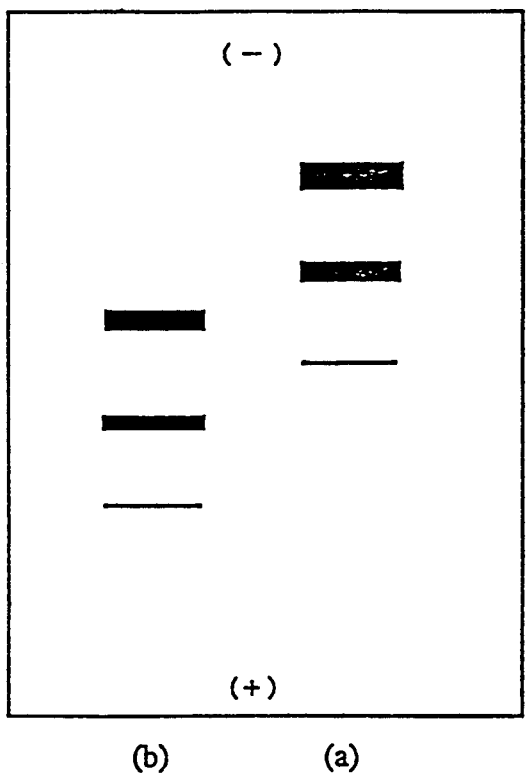
FIG. 6 shows schematic electrophorograms of (a) the SOD used in Example 6 and (b) the SOD derivative obtained in Example 6.
Figure 7:
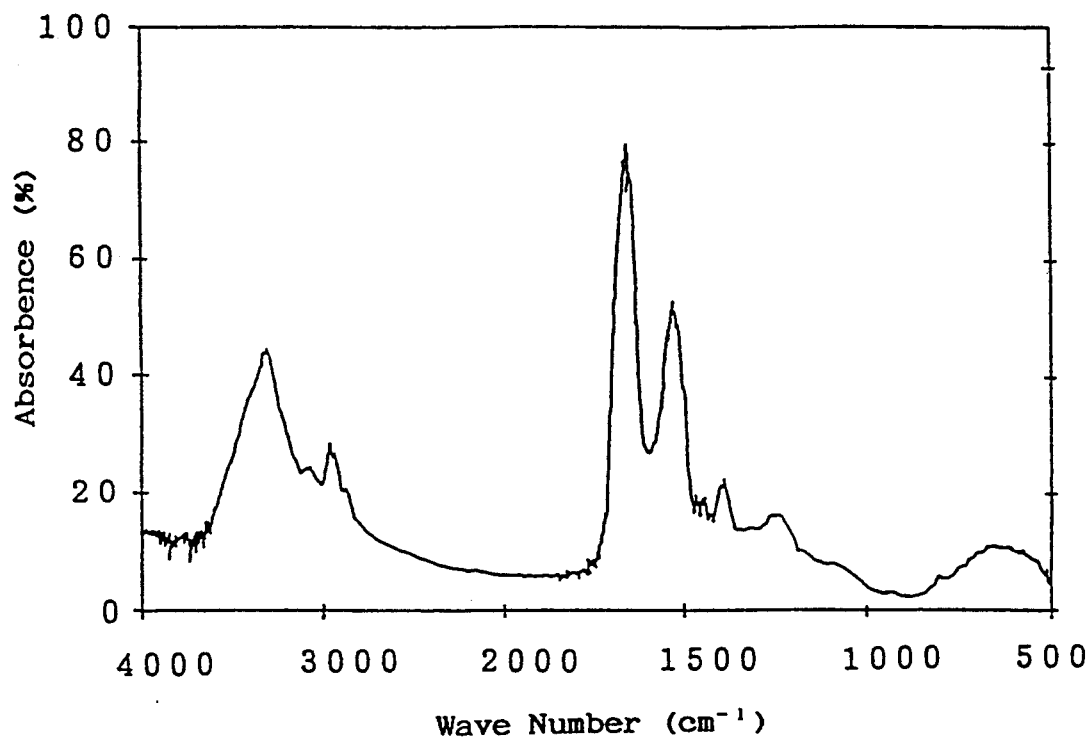
FIG. 7 shows an IR-spectrum of the SOD derivative obtained in Example 6.

The schematic electrophorograms of the SOD used and the SOD derivative obtained are shown in FIG. 6 (a) and (b). The obtained SOD derivative was identified, in the same manner as in Example 4, to be that comprising SOD with its 2 SH groups each bonded to 1 molecule of 22-maleimidododocosanoic acid. FIG. 7 shows an IR spectrum of the SOD derivative.

TEST EXAMPLE 1

Plasma Clearance of SOD Derivatives

Figure 8:
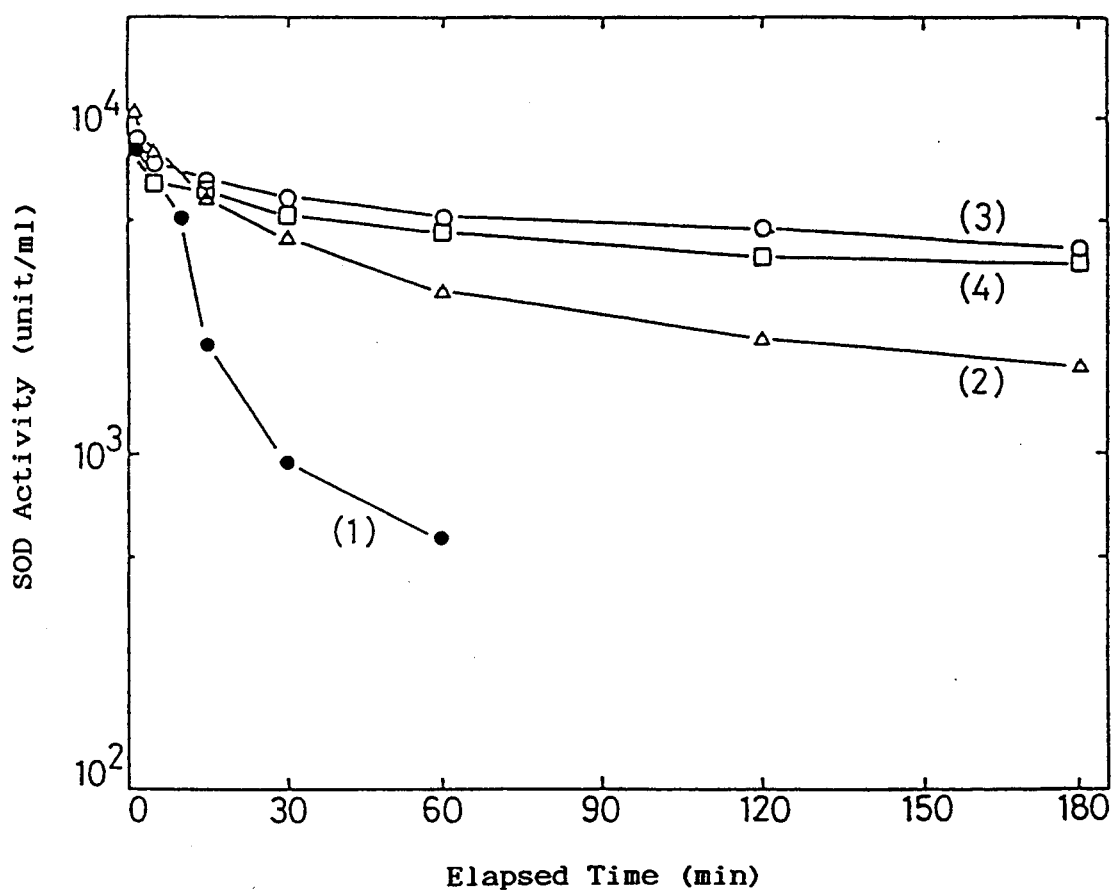
FIG. 8 shows the time courses of the plasma concentrations in Test Example 1, wherein (1), (2), (3) and (4) are for unmodified SOD, the SOD derivative obtained in Example 4, the SOD derivative obtained in Example 5 and the SOD derivative obtained in Example 6, respectively.

Under pentobarbital anesthsia, rats (Wistar strain, male, 7 weeks of age, body weight about 200 g) were cannulated into the femoral vein and were heparinized intravenously (1000 U/ml, 0.2 ml/rat). Then, a specimen solution of SOD or SOD derivative in saline (10 mg/ml) was injected into the femoral vein of each rat in an amount of 0.2 ml/rat. At timed intervals, 0.2 ml blood samples were collected from the femoral vein and the time courses of plasma SOD concentrations were determined by measuring the SOD activities in plasma. The results are shown in FIG. 8.

TEST EXAMPLE 2

Effect of SOD Derivative on Acute Gastric Mucosal Lesion

Male SD rats (body weight: about 200 g) were fasted overnight and were placed in restraint cages in 2 groups each of 6 animals. The cages were vertically immersed upto the level of xyphoid process in water at 22° C. After 6 hours of stress loading, the cages were taken out from the water and the rats were exsanguinated. Their stomachs were fixed by 10% formalin. After this fixation, the lengths of linear ulcers were totaled and the sum was expressed as the ulcer index.

Rats in the control group received 0.5 ml each of saline, while rats in the test group received 0.2 ml each of a solution of the SOD derivative obtained in Example 4 and weighing 2 mg/rat, all by intravenous route 5 minutes before restraint water-immersion.

The obtained results are shown in Table 2

TABLE 2

|  | Ulcer index |
|---|---|
| Control | 30.5 ± 15 |
| Test | 11.8 ± 9.5 |

As is apparent from Table 2, the SOD derivative exhibited an excellent anti-ulcer activity.

TEST EXAMPLE 3

Effect of SOD Derivative on Rat Postischemic Reperfusion Arrhythmias

Rats (Wistar strain, male, body weights 200–230 g) were fasted overnight. Under pentobarbital anesthesia (50 mg/kg body weight), the trachea was cannulated and artificial respiration was started using a volume of 1.5 ml/100g body weight and a rate of 60 strokes/min. The chest was opened by thoractomy and the pericardium was incised. The coronary artery was occulated by suction of the anterior descending branch of the left coronary artery at a site about 3 mm peripheral of the origin of the ramus circumflexus. The occlusion-reperfusion procedure was performed twice at a 30 minute interval; and after 15 minutes of the first reperfusion, each test compound was injected into the femoral vein in a dose of 5 mg/kg body weight (total volume 0.1 ml). As for the test compound, rats in the control groups received saline, while rats in the test groups received a solution of the SOD derivative obtained in Example 5 dissolved in saline. In each reperfusion procedure, the electrocardiogram (lead II) was continuously monitored for 30 minutes, and the duration of premature ventricular complexes (PVC), ventricular tachycardia (VT) and ventricular fibrillation (Vf) were measured. The obtained results are shown in Table 3.

TABLE 3

|  | Control (6 animals) | Test (5 animals) |
|---|---|---|
| Duration of PVC (sec) | 95 ± 62 | 85 ± 24 |
| Duration of VT (sec) | 112 ± 20 | 48 ± 24 |
| Duration of Vf (sec) | 465 ± 172 | 184 ± 160 |
| Incidence of Vf (%) | 100 | 40 |
| Mortality (%) | 66.7 | 20 |

As shown in Table 3, it is clear that the SOD derivative exhibited excellent anti-arrythmic activities.

Obviously, numerous modifications and variations of the present invention are possible in light of the above teachings. It is therefore to e understood that within the scope of the appended claims, the invention may be practiced otherwise than as specifically described herein.

What is claimed is:

1. An enzymatically active human superoxide dismutase derivative represented by the following general formula (I):

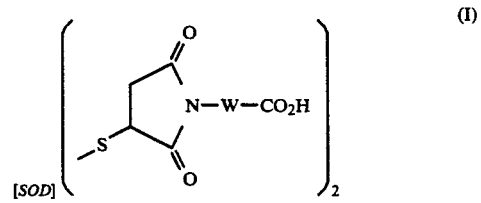

wherein [SOD] is a human superoxide residue derived by removal of two mercapto groups, and W is a divalent long chain hydrocarbon residue which may optionally be interrupted by one or more groups each independently selected from the group consisting of an oxygen atom, a sulfur atom and a group of —N(R)— (R being a lower alkyl group).

2. The enzymatically active human superoxide dismutase derivative of claim 1, wherein said human superoxide dismutase comprises human Cu·Zn—SOD, Mn—SOD, or Fe—SOD.

3. An enzymatically active human superoxide dismutase derivative which is produced by the reaction of a human superoxide dismutase with a long chain carboxylic acid maleimide represented by the following general formula (II)

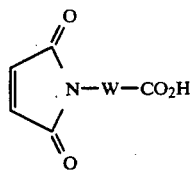

wherein W is a divalent long chain hydrocarbon residue comprising from about 9 to about 29 carbon atoms which may optionally be interrupted by one or more groups each independently selected from the group consisting of an oxygen atom, a sulfur atom and a group of —N(R)— (R being a lower alkyl group) and wherein said reaction is effected at a pH ranging from about 6 to 10.

* * * * *